United States Patent [19]

Yin

[11] Patent Number: 4,946,775
[45] Date of Patent: * Aug. 7, 1990

[54] COMPOSITION, KIT AND METHOD FOR ASSAYING HEPARIN AND A METHOD FOR MAKING THE COMPOSITION

[76] Inventor: E. Thye Yin, 2335 S. Hanley Rd., St. Louis, Mo. 63144

[*] Notice: The portion of the term of this patent subsequent to Jul. 25, 2006 has been disclaimed.

[21] Appl. No.: 363,783

[22] Filed: Jun. 9, 1989

Related U.S. Application Data

[63] Continuation of Ser. No. 236,857, Aug. 26, 1988, Pat. No. 4,851,336, which is a continuation of Ser. No. 14,261, Feb. 11, 1987, abandoned, which is a continuation of Ser. No. 772,846, Sep. 5, 1985, abandoned.

[51] Int. Cl.$^5$ .................. C12Q 1/56; G01N 21/75; G01N 33/86
[52] U.S. Cl. .................. 435/13; 422/61; 436/69; 436/94; 436/166
[58] Field of Search .................. 436/69, 93, 94, 111, 436/119, 127, 128, 129, 131, 166; 435/13; 422/61

[56] References Cited

U.S. PATENT DOCUMENTS

| | | | |
|---|---|---|---|
| 3,179,567 | 4/1965 | Owren | 435/13 |
| 3,293,134 | 12/1966 | Lenahan et al. | 435/13 |
| 3,799,885 | 3/1974 | Dennis et al. | 436/94 |
| 4,067,777 | 1/1978 | Innerfield et al. | 435/13 |
| 4,202,872 | 5/1980 | Collen | 436/804 X |
| 4,234,682 | 11/1980 | Bartl et al | 435/13 |
| 4,409,327 | 10/1983 | Bartl et al. | 435/13 |
| 4,622,389 | 11/1986 | Nagasawa et al. | 435/13 X |
| 4,663,146 | 5/1987 | Morser et al. | 422/61 X |
| 4,672,030 | 6/1987 | Witt | 435/13 |

FOREIGN PATENT DOCUMENTS

| | | | |
|---|---|---|---|
| 0107383 | 5/1984 | European Pat. Off. | 435/13 |
| 1010562 | 4/1983 | U.S.S.R. | 436/69 |

OTHER PUBLICATIONS

Sigma Techincal Bulletin No. 870, "A Clotting Procedure for the Quantitative Determination of Heparin in Plasma", Published by Sigma Chemical Company, 1982.
Yin et al., J. Lab. Clin. Med., vol. 81, No. 2, pp. 298–310, 1923.
Fareed et al., Clin. Chem., vol. 29, No. 2, pp. 225–236, 1983.
Yin et al., Chemical Abstracts, vol. 93, No. 3, Abstract No. 93:22057W. 1980.

Primary Examiner—Robert J. Hill, Jr.
Attorney, Agent, or Firm—Fred Philpitt

[57] ABSTRACT

A composition, kit and method for determining the concentration of heparin in a blood plasma sample and a method for making the composition. The method includes incubating a blood plasma sample with a known amount of Factor $X_a$, combining the incubated product with an admixture of calcium chloride, brain phospholipids, and a buffered plasma fraction that has been produced by treating mammalian blood to substantially remove Factors II, VII, IX and X while retaining Factor V and fibrinogen, and measuring the time it takes for clotting to occur after combining the incubated product with the admixture.

4 Claims, 1 Drawing Sheet

TYPICAL CALIBRATION CURVE

BBL FIBROMETER USED

COMPOSITION, KIT AND METHOD FOR ASSAYING HEPARIN AND A METHOD FOR MAKING THE COMPOSITION

This is a continuation of application Ser. No. 236,857, filed Aug. 26, 1988, now Pat. No. 4,851,336, which is a continuation of application Ser. No. 014,261 filed Feb. 11, 1987, now abandoned, which in turn is a continuation of application Ser. No. 772,846 filed Sept. 5, 1985, now abandoned. The benefits of 35 USC 120 are claimed relative to these applications.

This invention pertains to an improved method for determining the amount of heparin in a blood sample, and compositions useful in connection with the method.

BACKGROUND

The determination of heparin establishes an important parameter for the supervision of heparin treatment which is often administered in the presence of a threat of thrombosis. Heparin forms with antithrombin III (AT III) a complex which inhibits the proteolytic activity of thrombin. Since thrombin catalyzes the formation of fibrin from fibrinogen, the thrombin activity is responsible for the coagulation of blood or plasma and hence also for the fibrin clots which form in thrombosis. Heparin treatment is often applied in the presence of a threat of thrombosis (e.g. before surgical interventions). A precise adjustment of heparin concentration is therefore extremely important. If the dose is too low, there is the danger of thrombosis or embolism, which can result in death. Excessively high heparin concentrations, however, result in bleeding. The quantitative analysis of heparin, therefore, is one of the tests most frequently performed in the blood testing laboratory.

In 1973 Yin and co-workers developed the first quantitative assay method for the in vitro measurement of heparin in plasma based on Factor $X_a$ neutralization (J. Lab. Clin. Med. 81: 298, 1973). This assay method had the advantage over the methods known prior to 1973 in that it could detect less than 0.02 units of heparin per milliliter of plasma. However, the assay is cumbersome and time consuming to perform. It is a two-stage assay, and requires much manual manipulation. In the firststage of the assay, the patient's plasma sample is incubated with normal plasma, buffer, and a known excess of Factor $X_a$ for a predetermined time period, after which a sub sample from this primary reaction mixture is removed and assayed for Factor $X_a$ activity. The latter step constitutes the second-stage of the assay. Factor $X_a$ activity is measured by the addition of the test sample to another test tube, and to it calcium chloride, cephalin in bovine plasma are added separately in timed fashion. A commercial embodiment of this method is described in detail in Sigma Chemical Company Technical Bulletin No. 870 (as revised in January 1982). A copy of this bulletin is attached hereto and its disclosure is incorporated by reference.

THE PRESENT INVENTION

Figure 1:
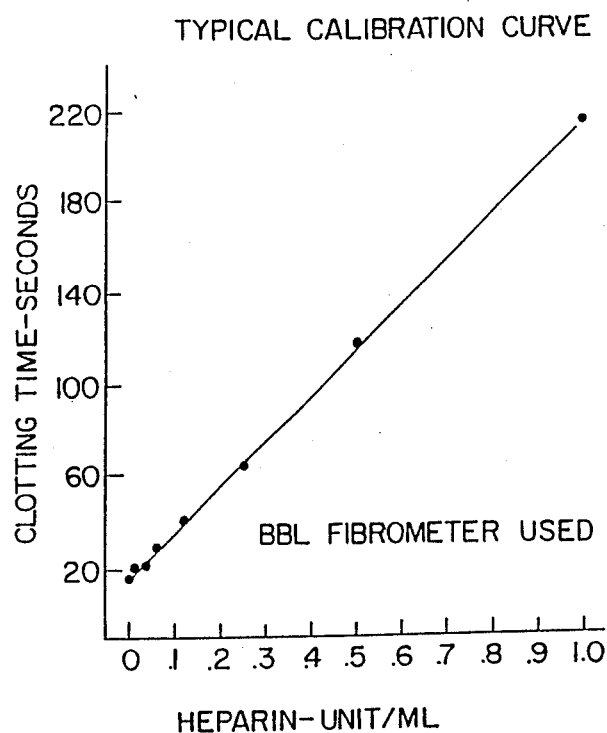
FIG. 1 shows a calibration curve of clotting time versus amount of heparin using the method of the present invention.

I have now developed an improved, simplified version of the above identified Yin et al method and the improved method involves (a) incubating an undiluted patient blood plasma sample with an amount of Factor $X_a$ which exceeds that which can be completely neutralized by the heparin in the patient blood sample (b) contacting the incubated product with a reagent containing an admixture of calcium chloride, phospholipids (e.g. brain cephalin) and a specially prepared buffered blood plasma fraction to thereby develop the appearance of a clot and (c) comparing the clotting time in step (b) with the clot times on an established calibration curve obtained by plotting clotting time versus heparin concentration to thereby determine the amount of heparin in the patient blood plasma sample.

Considered from one aspect the present invention involves a method for determining the amount of heparin in a blood plasma sample, which method comprises
(A) incubating the blood plasma sample for a fixed period of time with a known amount of Factor $X_a$, which known amount is in excess of the amount needed to react with all the heparin - AT III complexes in the blood plasma sample,
(B) combining the incubated product of step (A) with an admixture of
   (1) calcium chloride,
   (2) brain phospholipids, and
   (3) a buffered plasma fraction that has been produced by treating mammalian blood to substantially remove clotting Factors II, VII, IX and X while retaining clotting Factor V and fribrinogen,
said admixture being characterized by the fact that
   (a) it does not clot by itself for at least 24 hours at 37° C., and
   (b) it forms a firm clot in the presence of added thrombin, and
   (c) it contains at least 50% of Factor V that is present in one ml of normal human plasma, and
   (d) it provides a linear heparin dilution curve using a standard heparin preparation, and
(C) measuring the time it takes for clotting to occur after combining the incubated product of step (A) with said buffered admixture, which time is directly proportional to the concentration of heparin present in the blood plasma sample.

The method is suitably carried out with 100 microliters of a patient's blood plasma, 100 microliters of Factor $X_a$ and 100 microliters of the admixture set forth in (B) above.

The Factor $X_a$ can be prepared from bovine plasma by any method described in the literature. For example, Yin, E. T., Wessler, S., and Stoll, P., J. Biol.Chem.243: 112 (1968). The purified Factor $X_a$ is further lyophilized and stabilized in a buffer containing crystalline bovine serum albumin, polyethylene glycol, NaCl, and Tris (hydroxymethyl) aminomethane maleate, pH 7.5. Factor $X_a$ as described in the aforementioned SigmaBulletin No. 870 can be used.

Incubation of the patient's blood plasma and Factor $X_a$ preferably takes place at 37° C. for 60–160 seconds, and more preferably for a time period of 120 seconds.

The plasma fraction of (B) (3) is mammalian blood that is substantially free of Factors II, VII, IX and X but which still contains Factor V and fibrinogen, and can be produced by the steps of
   (i) treating mammalian blood with an anticoagulant and then removing blood cells to produce a plasma,
   (ii) subjecting the plasma from step (i) to at least one separation step to remove coagulation Factors II, VII, IX and X, and recovering the resulting plasma, (iii) subjecting the plasma resulting from step (ii) to at least one further separation step and recovering therefrom a protein fraction containing fibrinogen and coagulation Factor V, and (iv) treating the protein fraction recovered from step (iii) to remove therefrom soluble ammonium salt and insoluble proteins and recovering a clear plasma fraction, and (v) buffering the clear plasma fraction obtained from step (iv) so as to obtain a buffered plasma fraction.

The buffered plasma fraction produced by steps (i)–(v) is admixed with calcium chloride and brain phospholipids and the resulting admixture has the characteristics (a)–(d) set forth above.

In step (i) 9 volumes of the mammalian blood can be treated with one volume of 3.8% sodium citrate solution to effect anticoagulation and then centrifuged at $2500 \times g$ to remove blood cells. Bovine blood is preferred.

In step (ii) the separation can be effected by adding to 1000 ml of plasma from step (i) 7.35 gm of trisodium citrate, stirring to dissolve the citrate, followed by the addition of 20.825 gms of barium chloride (sufficient to achieve an overall barium chloride concentration of about 0.1 M in the plasma mixture) at room temperature over a period of 1–2 hours, and the heavy precipitate thus formed with the aid of barium citrate can be removed by the centrifugation of the plasma mixture at $3000 \times g$ for 20 minutes (the heavy precipitate containing Factors II, VII, IX and X) leaving a clear plasma supernatant.

Instead of using citrate blood and adsorbing the Factors II, VII, IX and X with a barium-citrate salt, one could employ aluminum hydroxide, or barium sulfate, or any other method which will remove these clotting proteins, e.g. ion exchanger column chromatography. If barium sulfate is used blood collected in sodium or potassium oxalate is used instead of sodium citrate.

In step (iii) the separation can take the form of fractionation with solid ammonium sulfate at a concentration of approximately 270 gm per liter of the plasma at room temperature. If the resulting plasma mixture is allowed to sit at room temperature for 1–2 hours, and then centrifuged at $4000 \times g$ for 15 minutes at room temperature, a precipitated protein fraction can be obtained. The concentration of ammonium sulfate of 270 gm/l corresponds to a 40–45% saturated solution. At a salt concentration of about 30% saturation fibrinogen precipitates out; as the salt concentration increases above 30% saturation to the area of 40% saturation the Factor V proteins precipitate out, as well as some other as yet unidentified proteins. Thus, whereas I have found that an ammonium sulfate concentration of 270 gm/l is quite suitable in precipitating out fibrinogen and Factor V proteins, I feel that lowering or increasing this concentration would still result in a quite satisfactory protein fraction. The use of ammonium sulfate to precipitate fibrinogen is described in a number of publications, e.g. "The Biochemistry of Blood Coagulation" by T. Astrup, in Acta Physiologica Scandanavia, Supplement 21,1944. The use of ammonium sulfate for the fractionation of Factor V is also described in a number of publications, e.g. the publication "Human Blood Coagulation and Its Disorders" edited by Biggs & MacFarlane, p. 54, 3rd edition 1962.

Instead of using ammonium sulfate to precipitate Factor V and fibrinogen, equivalent separation might also be achieved with alcohol or column chromatography on ion exchangers, or gel filtration based on molecular size sieving principles.

In step (iv) the protein precipitate from step (iii) is harvested and dissolved in a volume of distilled water equal to 30–40% of the original plasma volume. This "plasma fraction" is then dialysed against 0.9% NaCl solution until no ammonium ion is present in the fraction. The dialysed plasma fraction is clarified by centrifugation at $3000 \times g$ for 15 minutes at room temperature.

In step (v) the clear plasma fraction from step (iv) can be buffered to a pH of 7.5 by mixing nine volumes of it with one volume of a solution containing 2.50 gm polyethyleneglycol, 90.0 gm.NaCl, 98.88 gm. Tris-maleate per liter of distilled water.

To the buffered-plasma fraction resulting from steps (i)–(v) calcium chloride is added to a final calcium chloride concentration of 0.025M., followed by the addition of brain phospholipids, such as the cephalin preparation of Bell, W. N. and Alton, H. G., Nature, 174:880(1954). The amount of cephalin required to be added to the "plasma fraction" will depend on the concentration of Factor $X_a$ chosen for the assay. For example, the more concentrated the Factor $X_a$ is in the assay system, the less amount of cephalin is needed, and vice versa.

If calcium chloride and phospholipid solutions are mixed together they will ordinarily quickly precipitate. In accordance with the present invention it has been discovered that precipitation can be avoided if these substances are mixed together in the presence of the buffered plasma fraction that results from steps (i)–(v). The resulting admixture is characterized by the fact that (a) it does not clot by itself for at least 24 hours at 37° C., and (b) it forms a firm clot in the presence of added thrombin, and (c) it contains at least 50% of Factor V that is present in one ml of normal human plasma, and (d) it provides a linear heparin dilution curve using a standard heparin preparation.

I have found it convenient to collect a blood specimen by clean venepuncture in a plastic tube containing 3.8% sodium citrate. The ratio of blood to anticoagulant is 9:1. The citrated blood is then centrifuged within two hours of collection at $4000 \times g$ for 20 minutes, at +5 to +20° C. The platelet-poor plasma is carefully removed and either stored for up to 24 hours at +5° C. or frozen if it is not to be tested immediately.

For manual testing the equipment that is recommended includes $12 \times 75$ mm glass test tubes, pipettes to deliver 0.1 ml, distilled water, two stopwatches and a 37° C. water bath. If a clot detector machine is to be used, such as a BBL Fibrometer, a 0.3 ml probe is employed.

Prior to testing it has been found desirable to (a) prewarm a convenient volume of said admixture (B) for at least 5 minutes at 37° C. and it can be left at this temperature for up to 2 hours, (b) prewarm the plasma to be tested at 37° C. for 1–10 minutes, (c) prewarm the clotting vessels (e.g. the test tubes or fibrocups) at 37° C., (d) maintain the Factor $X_a$ solution at room temperature (25° C.) for up to 8 hours.

As noted above, it has been found preferable to carry out the assay at 37° C.$\pm 0.5°$.

The three steps that are followed in the usual assay include:
- Step 1—pipetting 0.1 ml of undiluted test plasma into a clotting tube,
- Step 2—delivering 0.1 ml Factor $X_a$ to Step 1, and simultaneously starting the first stopwatch, mixing well,
- Step 3—Exactly 120 seconds after the addition of Factor $X_a$ in Step 2, adding 0.1 ml of the admixture used in (B) above and simultaneously starting the second stopwatch.

The number of seconds it takes for the above mixture (steps 1-3) to form a solid clot is noted and can be converted to units of heparin per ml of plasma using a standard heparin calibration curve such as is shown in FIG. 1. The methods for preparing such calibration curves are well known in the art (e.g. the aforementioned Sigma Technical Bulletin 870).

The following examples will serve to illustrate the invention:

EXAMPLE 1

Nine liters of bovine blood was anticoagulated with one liter of 3.8% sodium citrate solution and then centrifuged at 2500×g to remove blood cells. To one liter of the resulting plasma was added 7.35 gms of trisodium citrate, which was stirred to dissolve the citrate, followed by the addition of 20.825 gms of solid barium chloride at room temperature over a period of about 90 minutes. The heavy precipitate which formed was removed by centrifugation of the plasma mixture at 3000×g for about 20 minutes leaving a clear plasma supernatant. 270 g of solid ammonium sulfate was added to the clear plasma supernatant at room temperature and allowed to set for 90 minutes and then centrifuged at 4000×g for 15 minutes, and a precipitated protein fraction obtained. The recovered precipitated protein fraction was dissolved in 350 ml of distilled water and then dialysed against a 0.9 NaCl solution until all ammonium ions had been removed. The dialysed plasma fraction was then clarified by centrifugation at 3000×g for 15 minutes at room temperature and then buffered to a pH of 7.5 by mixing nine volumes of it with one volume of a solution containing 2.5 gm of polyethylene glycol, 90.0 gm of NaCl, 98.88 gm of trismaleate, dissolved in 1 liter of distilled water. Calcium chloride was added to this buffered plasma fraction to achieve a calcium chloride concentration of 0.025M, whereafter cephalin [prepared by Bell and Alton, Nature, 174:880 (1954)] was added in a volume ratio of one volume of such cephalin to 99 volumes of the buffered plasma fraction to which calcium chloride had already been added. The resulting admixture served as one of the assay materials for my method and Factor $X_a$ served as the other assay material for my method.

EXAMPLE 2

In an environment maintained at 37° C. 0.1 ml of an undiluted test plasma containing an unknown amount of heparin was pipetted into a clotting tube. To it was delivered 0.1 ml of Factor $X_a$ (obtained by the aforementioned method of Yin et al) with mixing and at the time of delivery a stopwatch was started. Exactly 120 seconds after said addition of Factor $X_a$, 0.1 ml of the admixture of Example 1 was added and a second stopwatch was started. The clotting time was observed to be 45 seconds which a calibration curve indicated meant a heparin content of 0.15 units/m of plasma.

EXAMPLE 3

The procedure of Example 2 was followed except that the Factor $X_a$ used was Activated Factor X Reagent, Stock No. 870-10 from the Sigma Chemical Company of St. Louis, Missouri. Results comparable to that of Example 2 were obtained.

In order to decrease the clotting time in Example 2 the concentration of cephalin in Example 1 can be increased or the Factor $X_a$ concentration in Example 2 can be increased.

I contemplate that my invention can be made available in kit form that would comprise in a freeze-dried form, (A) a container of Factor $X_a$ and (B) a container of an admixture of calcium chloride, brain phospholipids and a buffered plasma fraction that has been produced by treating mammalian blood to substantially remove clotting factors II, VII, IX and X while retaining clotting factor V and fibrinogen. The components (A) and (B) are preadjusted so that when employed in the assay they will provide optimal sensitivity to the heparin in blood plasma samples.

Whereas my invention has been specifically discussed in connection with heparin, it should also be understood that the invention is also applicable to heparin-like compounds and it is therefore to be understood that the term "heparin" herein includes heparin and heparin-like compounds whether they be natural, synthetic, high or low molecular weight heparin fractions or fragments.

What is claimed is:

1. A method for determining the concentration of heparin in a blood plasma sample which comprises
    (A) incubating the blood plasma sample for a limited period of time with a known amount of Factor $X_a$, to form an incubated product which known amount is in excess of the amount needed to react with all heparin - AT III complexes in the blood plasma sample within a given time period,
    (B) combining the incubated product of step (A) with an admixture of
        (1) calcium chloride,
        (2) brain phospholipids, and
        (3) a buffered plasma fraction that has been produced by treating mammalian blood to substantially remove clotting Factors II, VII, IX and X while retaining clotting Factor V and fibrinogen,
    said admixture being characterized by the fact that
        (a) it does not clot by itself for at least 24 hours at 37° C., and
        (b) it forms a firm clot in the presence of added thrombin, and
        (c) it contains at least 50% of Factor V that is present in one ml of normal human plasma, and
        (d) it provides a linear heparin dilution curve using a standard heparin preparation, and
    (C) measuring the time it takes for clotting to occur after combining the incubated product of step (A) with said admixture, which clotting time is directly proportional to the concentration of heparin present in the blood plasma sample.

2. An assay composition comprising an admixture of
    (1) calcium chloride,
    (2) brain phospholipids, and
    (3) a buffered plasma fraction that has been produced by treating mammalian blood to substantially remove clotting Factors II, VII, IX and X while retaining clotting Factor V and fibrinogen, said admixture being characterized by the fact that
  (a) it does not clot by itself for at least 24 hours at 37° C., and
  (b) it forms a firm clot in the presence of added thrombin, and
  (c) it contains at least 50% of Factor V that is present in one ml of normal human plasma, and
  (d) it provides a linear heparin dilution curve using a standard heparin preparation.

3. A kit for determining the amount of heparin in a selected blood plasma sample which comprises
  (A) a container of a first reagent which comprises Factor $X_a$, the amount of the Factor $X_a$ being in excess of the amount needed to react with all heparin - AT III complexes in the selected blood sample within a given time period,
  (B) a container of a second reagent which comprises an admixture of
    (1) calcium chloride,
    (2) brain phospholipids, and
    (3) a buffered plasma fraction that has been produced by treating mammalian blood to substantially remove clotting Factors II, VII, IX and X while retaining clotting Factor V and fibrinogen,
  said admixture being characterized by the fact that
    (a) it does not clot by itself for at least 24 hours at 37° C., and
    (b) it forms a firm clot in the presence of added thrombin, and
    (c) it contains at least 50% of Factor V that is present in one ml of normal human plasma, and
    (d) it provides a linear heparin dilution curve using a standard heparin preparation.

4. A method for producing an assay composition comprising
  (a) treating a cell-free mammalian blood plasma to remove Factors II, VII, IX and X and recovering a clear plasma supernatant,
  (b) subjecting said clear plasma supernatant to a protein fractionation treatment and recovering a protein fraction that contains fibrinogen and Factor V,
  (c) subjecting the protein fraction of step (b) to a purification treatment to remove therefrom any soluble ammonium salt and insoluble proteins, and obtaining a clear plasma fraction,
  (d) buffering said clear plasma fraction to obtain a buffered plasma fraction,
  (e) admixing said buffered plasma fraction with calcium chloride and brain phospholipids, and recovering an admixture that is characterized by the fact that
    (1) it does not clot by itself for at least 24 hours at 37° C., and
    (2) it forms a firm clot in the presence of added thrombin, and
    (3) it contains at least 50% of Factor V that is present in one ml of normal human plasma, and
    (3) it provides a linear heparin dilution curve using a standard heparin preparation.

* * * * *